United States Patent
Starnes

(10) Patent No.: US 9,017,288 B1
(45) Date of Patent: Apr. 28, 2015

(54) CATHETER WITH INTEGRATED PRE-SLIT CANNULA DIAPHRAGM

(75) Inventor: Stacy E. Starnes, Mulhall, OK (US)

(73) Assignee: Proteckt Catheters, LLC, Mulhall, OK (US)

(*) Notice: Subject to any disclaimer, the term of this patent is extended or adjusted under 35 U.S.C. 154(b) by 964 days.

(21) Appl. No.: 12/342,288

(22) Filed: Dec. 23, 2008

Related U.S. Application Data

(62) Division of application No. 11/201,636, filed on Aug. 10, 2005, now Pat. No. 7,469,458.

(60) Provisional application No. 60/601,001, filed on Aug. 11, 2004.

(51) Int. Cl.
*A61M 5/178* (2006.01)
*A61M 25/00* (2006.01)

(52) U.S. Cl.
CPC .................................. *A61M 25/0043* (2013.01)

(58) Field of Classification Search
CPC ........... A61B 17/3415; A61B 17/3498; A61B 17/3421; A61B 17/3462; A61B 5/150496; A61M 2039/0646; A61M 2039/1072; A61M 25/06; A61M 25/0668; A61M 39/04; A61M 39/0613; A61M 2039/0036; A61M 2039/0072; A61J 1/1406; A61J 2001/2044
USPC ............... 604/158, 162, 163, 164.01, 164.08, 604/167.01, 167.02, 167.03, 167.04, 604/168.01, 244, 246, 256, 263, 533, 534, 604/535, 537, 538, 539, 905
See application file for complete search history.

(56) References Cited

U.S. PATENT DOCUMENTS

| | | | |
|---|---|---|---|
| 4,143,853 A * | 3/1979 | Abramson | 251/149.1 |
| 4,387,879 A * | 6/1983 | Tauschinski | 251/149.1 |
| 4,673,393 A | 6/1987 | Suzuki et al. | |
| 4,842,591 A * | 6/1989 | Luther | 604/537 |
| 4,895,565 A | 1/1990 | Hillstead | |
| 4,917,669 A * | 4/1990 | Bonaldo | 604/192 |
| 4,966,588 A | 10/1990 | Rayman et al. | |
| 5,085,645 A * | 2/1992 | Purdy et al. | 604/167.03 |
| 5,199,948 A | 4/1993 | McPhee | |
| 5,295,658 A | 3/1994 | Atkinson et al. | |
| 5,322,516 A * | 6/1994 | Brugger | 604/192 |
| 5,441,487 A * | 8/1995 | Vedder | 604/167.03 |
| 5,843,046 A * | 12/1998 | Motisi et al. | 604/256 |
| 6,287,278 B1 * | 9/2001 | Woehr et al. | 604/110 |
| 6,699,221 B2 * | 3/2004 | Vaillancourt | 604/167.01 |
| 6,709,419 B2 * | 3/2004 | Woehr | 604/164.07 |
| 6,755,391 B2 * | 6/2004 | Newton et al. | 251/149.6 |
| 6,840,501 B2 * | 1/2005 | Doyle | 251/149.1 |
| 7,736,339 B2 * | 6/2010 | Woehr et al. | 604/164.08 |

(Continued)

*Primary Examiner* — Nicholas Lucchesi
*Assistant Examiner* — Diva K Chander
(74) *Attorney, Agent, or Firm* — Hall Estill Attorneys at Law; Daniel P. Dooley

(57) ABSTRACT

A pre-slit cannula diaphragm is integrated into a peripheral venous catheter to provide a cannula ready intravenous catheter with a cannula chamber closed to the environment, thereby reducing the risk to health-care providers from blood borne diseases and the risk to patients from airborne hazards. The cannula ready intravenous catheter includes a cylindrical housing that provides an uninterrupted smooth surface, for reducing skin irritation. A proximal end of the cylindrical housing provides a luer-type connector site, and a distal end of the cylindrical housing provides a catheter hub. The catheter hub supports a catheter tube, which extends from a distal end of the catheter hub.

14 Claims, 8 Drawing Sheets

(56) References Cited

U.S. PATENT DOCUMENTS

| | | | |
|---|---|---|---|
| 8,328,762 B2* | 12/2012 | Woehr et al. | 604/164.08 |
| 2001/0044607 A1* | 11/2001 | DeMichele et al. | 604/192 |
| 2002/0128604 A1* | 9/2002 | Nakajima | 604/164.01 |
| 2002/0147431 A1* | 10/2002 | Lopez et al. | 604/256 |
| 2003/0098430 A1* | 5/2003 | Leinsing et al. | 251/149.6 |
| 2004/0097888 A1* | 5/2004 | Gutierrez | 604/264 |

* cited by examiner

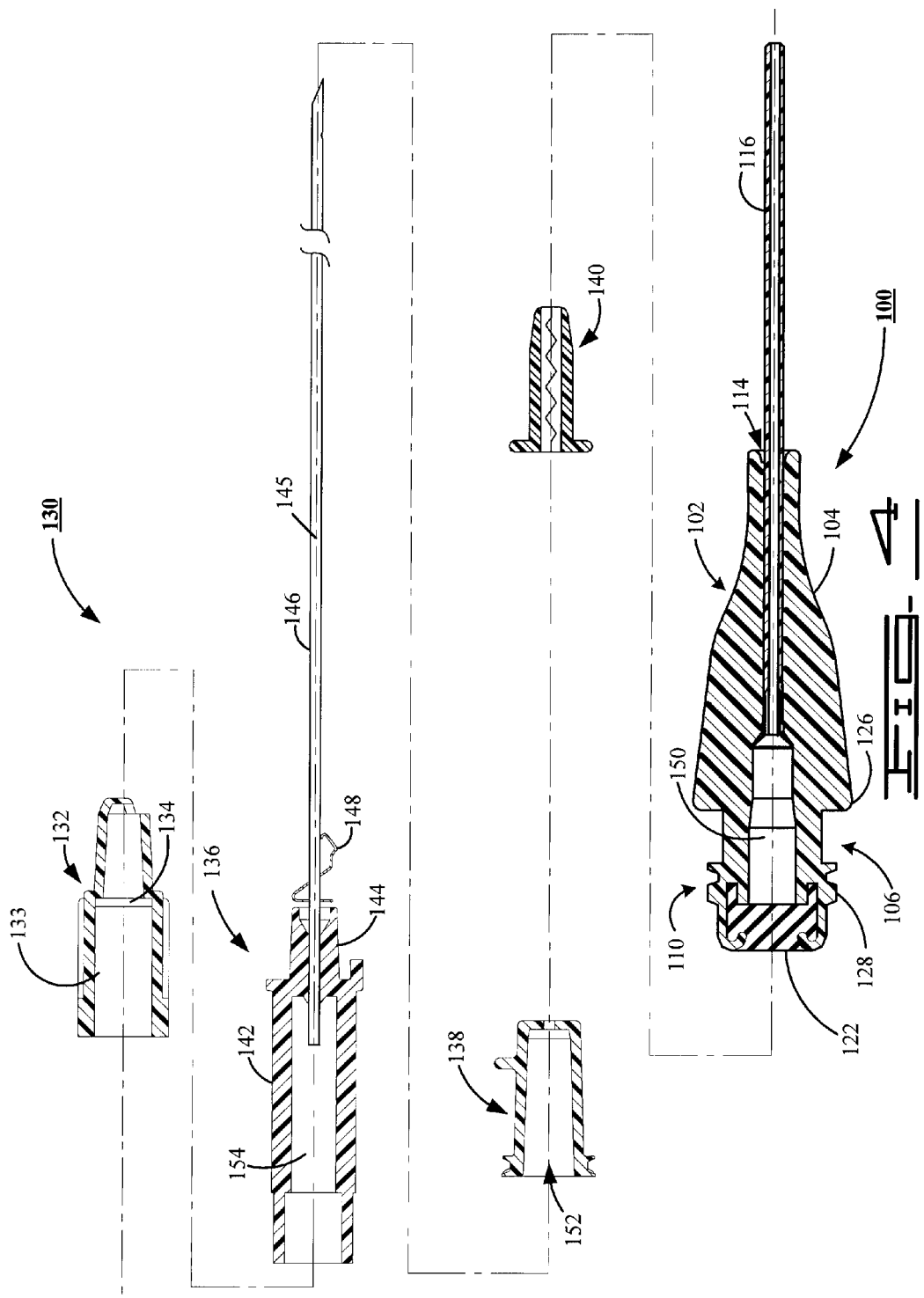

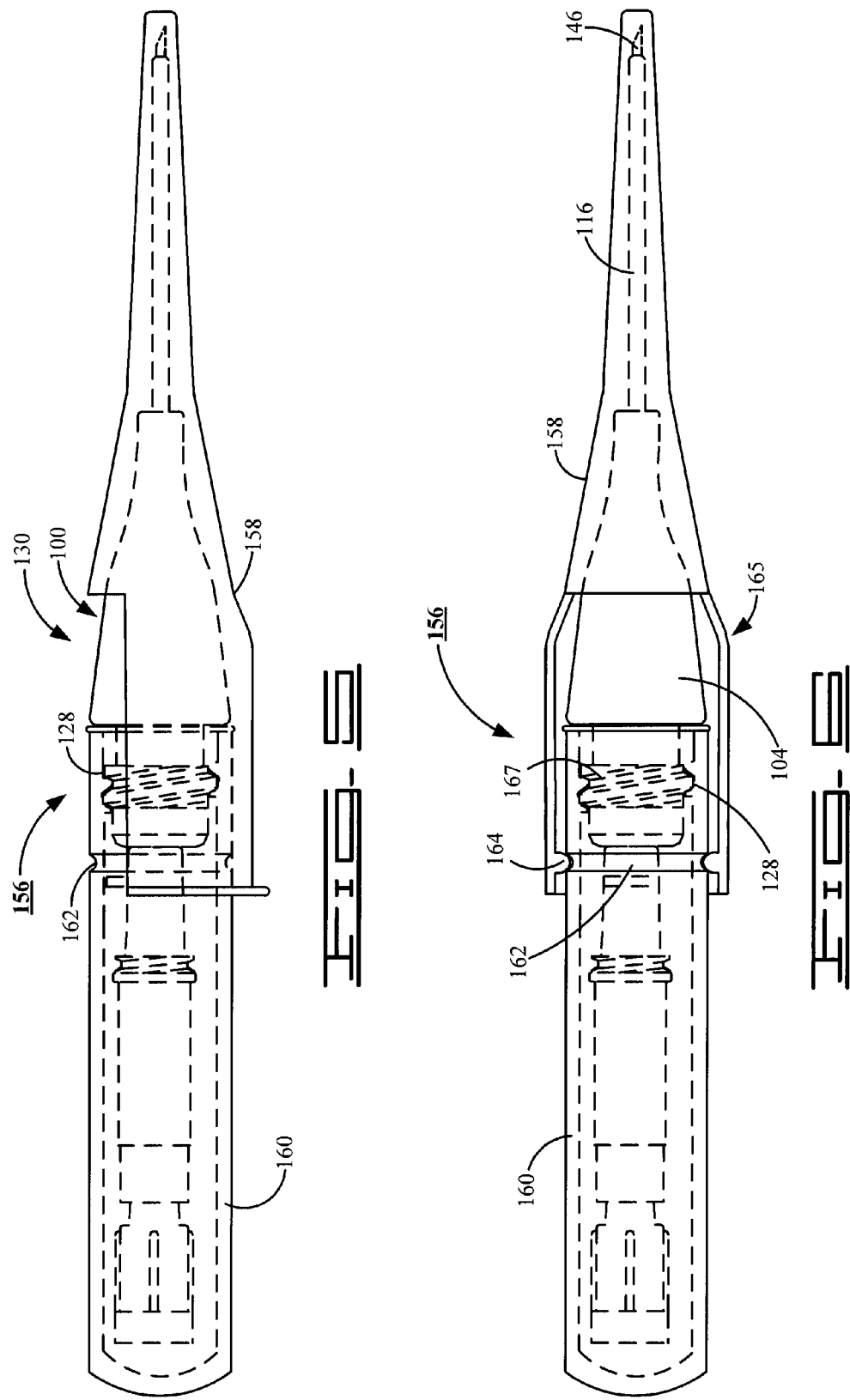

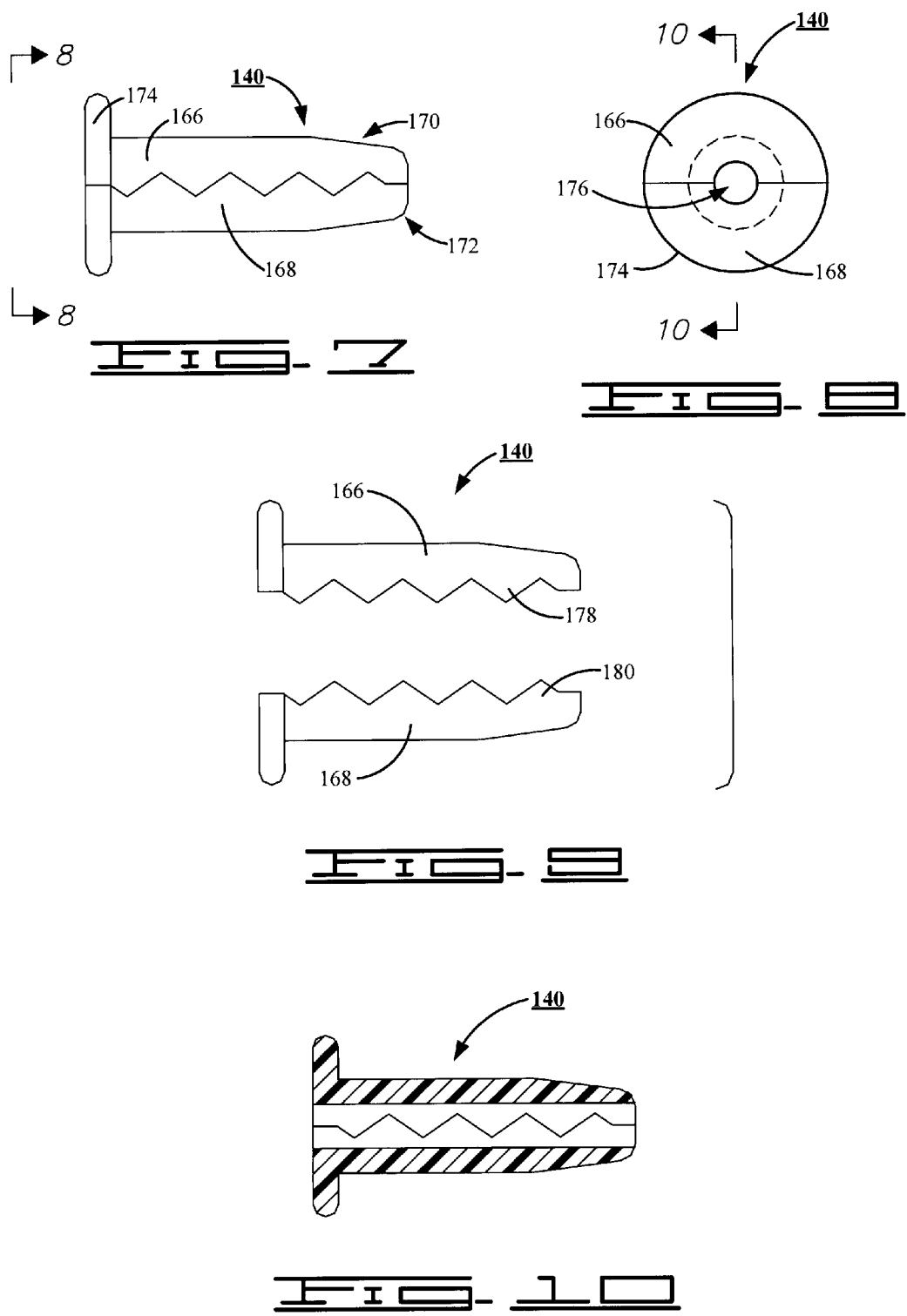

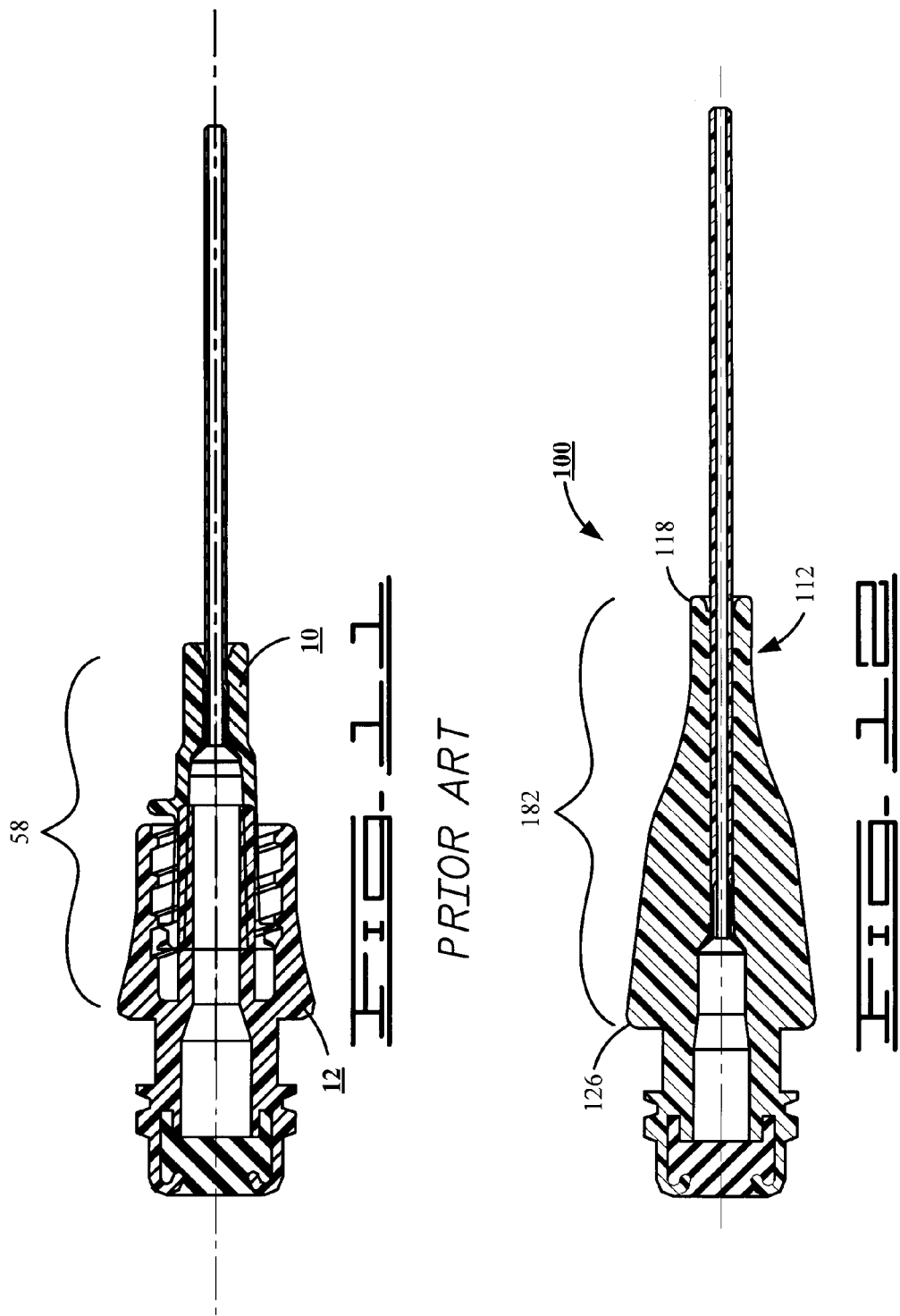

CATHETER WITH INTEGRATED PRE-SLIT CANNULA DIAPHRAGM

RELATED APPLICATIONS

This application is a divisional of U.S. patent application Ser. No. 11/201,636 filed Aug. 10, 2005, entitled "Method of Assembling A Catheter With Integrated Pre-Slit Cannula Diaphragm," now U.S. Pat. No. 7,469,458, issued Dec. 30, 2008, which claims priority to U.S. Provisional Application No. 60/601,001 filed Aug. 11, 2004, entitled "Catheter With Integrated Pre-Slit Cannula Diaphragm".

FIELD OF THE INVENTION

The claimed invention relates to the field of intravenous catheters; more particularly, but not by way of limitation, to a catheter with an integrated pre-slit cannula diaphragm.

BACKGROUND

Reducing exposure risks of both patients and healthcare providers during a procedure for starting an intravenous (IV) catheter is a continuing objective within the healthcare industry.

A reduction in the risk of infection of IV sites reduces the number of sites needed by patients, and reduces the need for treatment of patients with infected IV sites. By reducing the risk of contracting diseases by patients and healthcare providers during IV procedures, the probability of encountering complications during the patient's treatment is lessened; the health conditions for health care providers are improved; and healthcare delivery costs are reduced.

Accordingly, there is a continuing need for improved devices and procedures for the administration of patient IV's.

SUMMARY OF THE INVENTION

In accordance with preferred embodiments, an apparatus is provided with a cylindrical housing having a contoured central portion disposed between a proximal end and a distal end. The apparatus further includes an open fluid transfer conduit extending from the distal end, through the contoured central portion and out the proximal end. Additionally, the proximal end of the housing provides a luer-type connector site, while the distal end provides a catheter hub. The catheter hub supports a catheter tube, which extends from the catheter hub and communicates with the fluid transfer conduit. The apparatus further includes a pre-slit cannula diaphragm capping the fluid transfer conduit at a proximal end of the luer-type connector site. The luer-type connector site provides a shoulder and external male luer-type threads disposed between the shoulder and the diaphragm, and wherein the cylindrical housing provides an uninterrupted smooth surface of continuous decreasing diameter from the shoulder through the distal end of the catheter hub.

BRIEF DESCRIPTION OF THE DRAWINGS

FIG. 4 is a cross-sectional, elevational, and exploded view of an IV kit that includes the catheter with an integrated pre-slit injection site diaphragm of FIG. 2;

FIG. 5 is an elevational view of an assembled IV kit of FIG. 4 with an attached sheath and cover;

FIG. 6 is a plan view of the assembled IV kit of FIG. 4 with the attached sheath and cover;

FIG. 7 is an elevational view of a split faux-cannula assembly tool, which is not part of, but is used during, the assembly of the IV kit of FIG. 5;

FIG. 8 is an end, elevational view of the split faux-cannula assembly tool, of FIG. 7;

FIG. 9 is an exploded, elevational view of the split faux-cannula assembly tool, of FIG. 7;

FIG. 10 is a cross-sectional, elevational view of the split faux-cannula assembly tool, of FIG. 7;

FIG. 11 is a cross-sectional, elevational view of the prior art catheter in combination with its corresponding prior art pre-slit injection site diaphragm with cannula adapter of FIG. 1;

FIG. 12 is a cross-sectional, elevational view of the catheter with an integrated pre-slit injection site diaphragm of FIG. 2.

DETAILED DESCRIPTION

Reference will now be made in detail to one or more examples of the invention depicted in the figures. Each example is provided by way of explanation of the invention, and not meant as a limitation of the invention. For example, features illustrated or described as part of one embodiment may be used with another embodiment to yield still a different embodiment. Other modifications and variations to the described embodiments are also contemplated within the scope and spirit of the invention.

Figure 1:
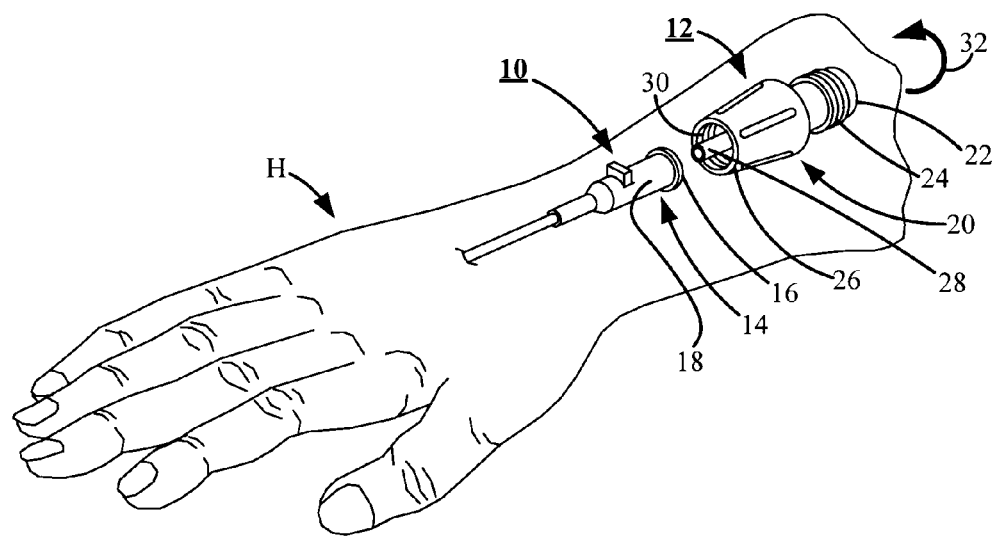
FIG. 1 is a view in perspective of a prior art catheter positioned in the hand of a patient and a corresponding prior art pre-slit injection site adapter.

Referring to the drawings, FIG. 1 shows a prior art peripheral venous catheter 10 in fluid flow communication with a vein in a hand H of a patient. Also shown is a pre-slit injection site 12, ready for coupling to the peripheral venous catheter 10. The catheter 10, at a proximal end 14, provides an external female luer-type thread 16 that interacts with the pre-slit injection site 12 via a cannula housing 18.

The pre-slit injection site 12 is formed with a cylindrical housing 20 having a first end 22 supporting external male luer-type threads 24. Adjacent a second end 26 is a hollow cylindrical fluid flow member (also referred to as "cannula") 28. The cannula 28 slidably engages a receiving member in the housing 18 of the catheter 10, thereby providing a sterile fluid flow coupling as is well known and conventional. A plurality of internal male luer-type threads 30 is carried by the housing 20 adjacent the second end 26. The threads 30 will engage external female luer-type thread 16 when the injection site 12 is rotated in a direction 32. When so coupled together, the catheter 10 and the injection site 12 provide a sealed coupling through which fluids may be injected into the vein of the hand H.

Figure 2:
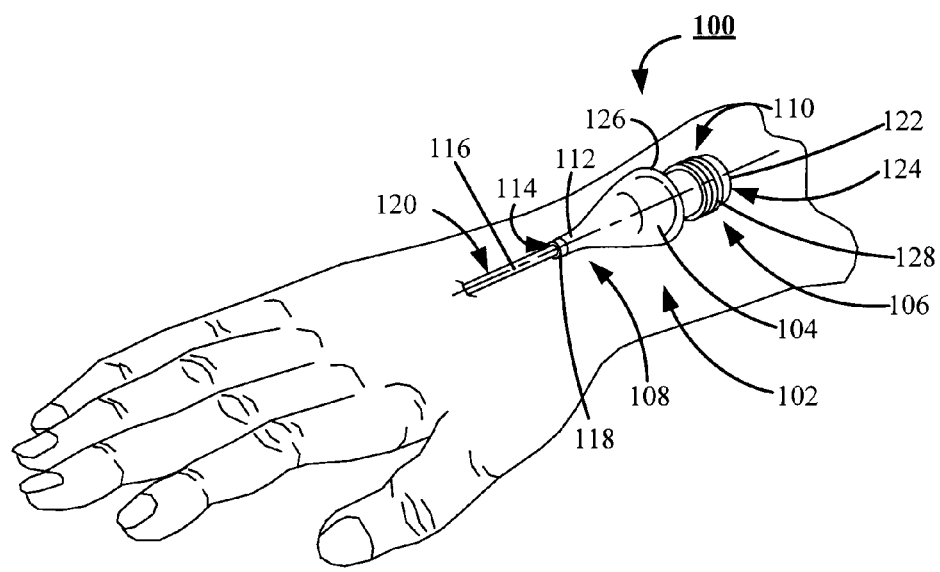
FIG. 2 is a view in perspective of a catheter with an integrated pre-slit injection site diaphragm of the present invention.

FIG. 2 shows a preferred embodiment of a peripheral venous catheter with an integrated pre-slit cannula diaphragm (also referred to herein as a "cannula ready IV") 100. The cannula ready IV 100, includes a cylindrical housing 102 having a contoured central portion 104 disposed between a proximal end 106 and a distal end 108. The proximal end 106 provides a luer-type connector site 110, formed by and integral to the cylindrical housing (as shown in FIG. 4), while the distal end 108 provides a catheter hub 112, formed by and integral to the cylindrical housing (as shown in FIG. 4). An open fluid transfer conduit 114 (shown in greater detail by FIG. 4) is substantially centered within and extends through the cylindrical housing 102.

The catheter hub 112 supports a catheter tube 116 extending from a distal end 118 of the catheter hub 112. An external surface 120 of the catheter tube 116 (shown in greater detail by FIG. 4) pressingly engages the fluid transfer conduit 114 provided by the cylindrical housing 102. A pre-slit cannula diaphragm 122 (shown in greater detail by FIG. 4) caps the fluid transfer conduit 114 at a proximal end 124 of the luer-type connector site 110.

The luer-type connector site 110 provides a shoulder 126, and external male luer-type threads 128 disposed between the shoulder 126 and the pre-slit cannula diaphragm 122. In contradistinction to the prior art of similar function, formed from the combination of the peripheral venous catheter 10 and the pre-slit injection site 12 (shown in greater detail by FIG. 11), the cannula ready IV 100 minimizes irritation of a patient's skin adjacent the IV site. Skin irritation minimization is attained through the presence of an uninterrupted smooth surface of continuous decreasing diameter from the shoulder 126 through the distal end 118 of the catheter hub 112 provided by the cylindrical housing 102.

Figure 3:
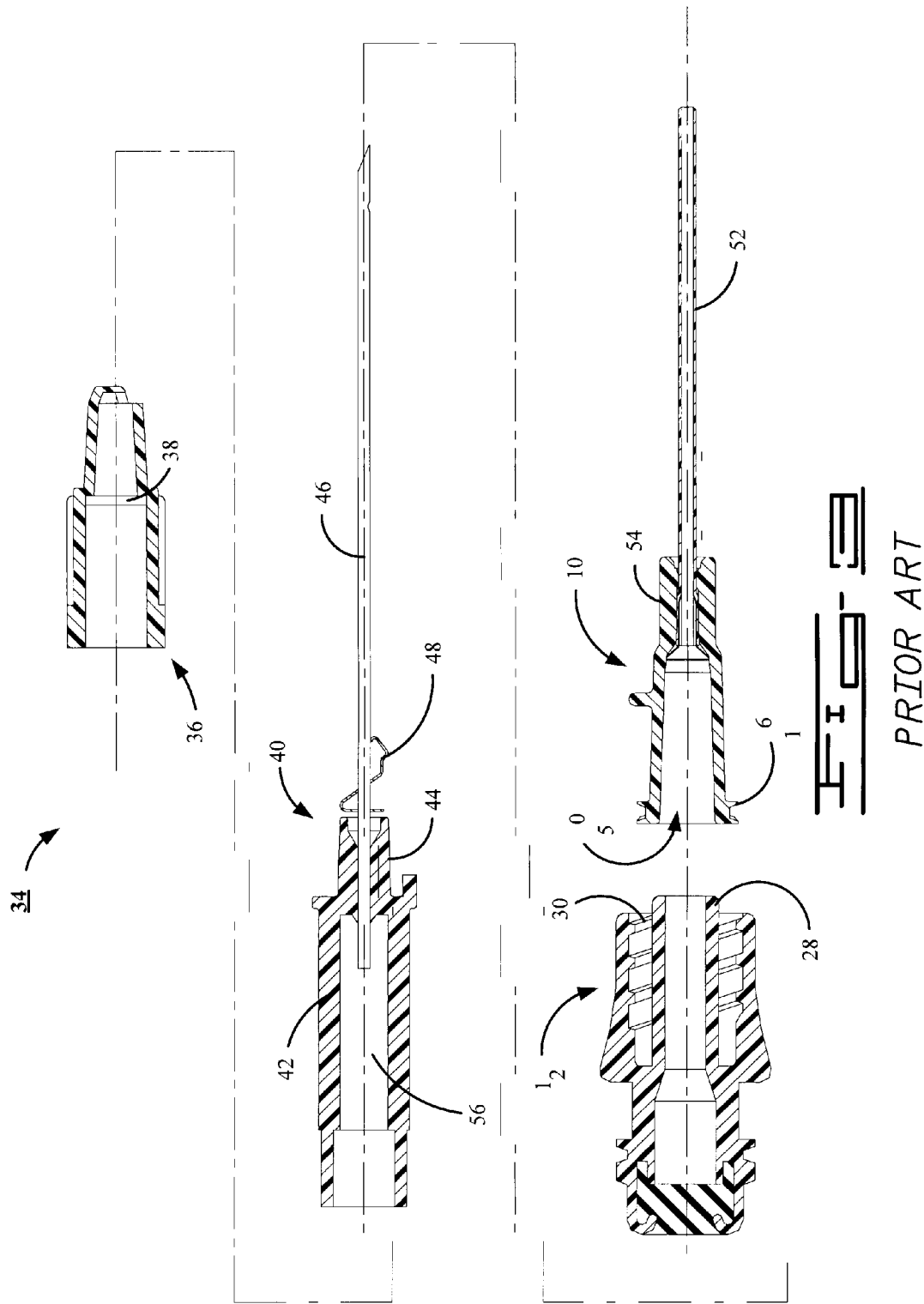
FIG. 3 is a cross-sectional, elevational, and exploded view of a prior art IV kit.

FIG. 3 shows a prior art needleless IV kit 34 that includes a pressure equalization member 36 supporting a HEPA type filter 38, a needle assembly 40, the pre-slit injection site 12, and the peripheral venous catheter 10. As is known in the art, the HEPA filter 38 removes small particles, such as micro-organisms, from the gaseous fluids that pass through the HEPA filter. The needle assembly 40 includes a blood chamber 42 with a needle hub 44 supporting an insertion needle 46; and a safety clip 48 slidingly attached to the insertion needle 46 to lessen inadvertent needlestick injuries.

The peripheral venous catheter 10 includes, a cannula chamber 50 and a catheter tube 52 supported by a catheter hub 54. Prior to administering the peripheral venous catheter 10 to a patient, the safety clip 48 and the needle hub 44 are confined within the cannula chamber 50, and the insertion needle 46 is supported within the catheter tube 52. Following a preparation of an insertion site, the insertion needle 46, together with the catheter tube 52, are inserted into the patient's vein.

Upon entry into the patient's vein, blood flows through the insertion needle 46 and into a collection chamber 56 of the blood chamber 42. With the needle assembly 40 held in a stationary position, the catheter tube 52 is slid along the insertion needle 46 to provide further migration of the catheter tube 50 within the patient's vein. When proper penetration has been attained, slight pressure is applied to the insertion site to prevent the further flow of blood into the collection chamber 56. The applied pressure also holds the peripheral venous catheter 10 stationary while the needle assembly 40 is removed and discarded.

With the peripheral venous catheter 10 held stationary, the cannula 28 of the pre-slit injection site 12 is inserted into the cannula chamber 50 of the peripheral venous catheter 10. The pre-slit injection site 12 is secured to the peripheral venous catheter 10 by engaging the external female luer-type thread 16 of the peripheral venous catheter 10 with the internal male luer-type threads 30 of the pre-slit injection site 12.

The amount of elapse time between removal of the needle assembly 40 and the securement of the pre-slit injection site 12 onto the peripheral venous catheter 10, is a time posing the greatest risk of exposure to disease for both the patient and the health-care provider. The health-care provider is exposed to blood borne diseases and the patient is exposed to airborne hazards because the cannula chamber 50 of the peripheral venous catheter 10 is open to the environment.

FIG. 4 shows an embodiment of a cannula ready IV kit 130 of the present invention. The cannula ready IV kit 130 includes: a pressure equalization member 132 providing a filter chamber 133, which supports a HEPA type filter 134; a needle assembly 136; a safety clip confinement member 138; a split faux-cannula assembly tool 140; and the preferred embodiment cannula ready IV 100. The needle assembly 136 includes: a blood chamber 142 with a needle hub 144 supporting an insertion needle 146; and the safety clip 148 slidingly attached to the insertion needle 146 to reduce the frequency of inadvertent needlestick injuries. The pressure equalization member 132 communicates with the blood chamber 142. The needle assembly 136 further has the blood chamber 142 providing a collection chamber 154.

As mentioned above, the HEPA filter removes micro-organisms from the gaseous fluids that pass through the HEPA filter. That is, as shown in FIG. 4, the pressure equalization member 132 comprises a filter medium, e.g., the HEPA type filter 134, disposed within the filter chamber 133 of the pressure equalization member, the filter medium facilitating transfer of gaseous fluids while precluding passage of micro-organisms.

The cannula ready IV 100 includes a cannula chamber 150 disposed between the pre-slit cannula diaphragm 122 and the catheter tube 116. Prior to administering the cannula ready IV 100 to a patient, the safety clip 148 is confined within the clip chamber 152, and the insertion needle 146 is supported within the catheter tube 116. Following preparation of the insertion site, the insertion needle 146, together with the catheter tube 116, are inserted into a patient's vein.

Upon entry of the insertion needle 146 and the catheter tube 116 into the patient's vein, blood flows from the patient's vein through a fluid transfer channel 145 of the insertion needle 146 and into the collection chamber 154. The needle assembly 136 interacts with the pre-slit cannula diaphragm 122, and the needle assembly facilitates access through a wall of a patient's vein for penetration of the catheter tube 116 into the vein. The pressure equalization member 132 assures that once the insertion needle 146 penetrates through the wall of the vein, the fluid from the vein is able to flow freely into the collection chamber 154. With the needle assembly 136 held in a stationary position, the catheter tube 116 is slid along the insertion needle 146 to provide greater penetration of the catheter tube 116 within the patient's vein. In other words, upon selectively inserting the insertion needle 146 into a patient, the insertion needle provides access to a vein of the patient for penetration of the catheter tube 116 into the vein of the patient. The needle hub 144 secures the inserted insertion needle 146 in a predetermined fixed position relative to the blood chamber 142. The blood chamber 142 collects fluid transferred from the vein through the fluid transfer channel 145. When proper penetration of the catheter tube 116 within the patient's vein has been attained, the cannula ready IV 100 is held stationary while the needle assembly 136 and the safety clip confinement member 138 are removed and discarded.

Because the pre-slit cannula diaphragm 122 is an integral component of the cannula ready IV 100, risk of exposure to disease for both the patient and the health-care provider is significantly reduced. The health-care provider is less exposed to blood borne diseases and the patient is less exposed to airborne hazards because the cannula chamber 150 of the cannula ready IV 100 is closed to the environment, which limits exposure to the micro-organisms that cause blood borne diseases and airborne hazards. As expected with an intravenous catheter, the cannula chamber 150 accommodates a corresponding cannula of a medical fluids transfer device.

That is, as shown in FIGS. 2 and 4, the cannula ready IV 100 includes the pre-slit cannula diaphragm 122 capping the fluid transfer conduit 114 at the proximal end 124 of the luer-type connector site 110, in which the luer-type connector site forms the mechanical connection feature adjacent the pre-slit cannula diaphragm, and wherein a diameter of the cylindrical housing 102 progressing from adjacent the mechanical connection feature through the distal end 118 of the cylindrical housing decreases, and in which the mechanical connection feature is formed by and integral to the cylindrical housing. The mechanical connection feature includes the external male luer-type threads 128 formed by and integral to the cylindrical housing 102. The shoulder 126 is disposed between the mechanical connection feature and the distal end 118 of the cylindrical housing 102, and the shoulder is formed by and integral to the cylindrical housing. The diameter of the cylindrical housing 102 progressing from adjacent the mechanical connection feature through the distal end 118 has a continuously decreasing uninterrupted smooth surface 182.

As one skilled in the art will recognize, the configuration of the needle assembly 136 is but one of many types of needle assemblies that may be selected for use with the cannula ready IV 100. The configuration of the needle assembly 136 was selected for clarity of presentation and for disclosure purposes only. The selected needle assembly 136 is foe disclosure enhancement and does not impose any limitations on the present invention.

FIG. 5 shows an elevational view of a sheath and cover assembly 156 that includes the catheter sheath 158 and a threaded needle assembly cover 160. The cover 160 is threaded onto the external male luer-type threads 128 of the luer-type connector site 110, and provides a sheath retention groove 162, which assures the catheter sheath 158 remains intact while the cannula ready IV kit 130 is removed from its sterilized package. In other words, threaded needle assembly cover 160 constrains movement of the needle assembly 136 relative to the pre-slit cannula diaphragm 122, when the threaded needle assembly cover 160 is lockingly engaged with the external male luer-type threads 128.

As can be seen by the plan view of the sheath and cover assembly 156, shown by FIG. 6, the catheter sheath 158 includes a retention ring 164, which interacts with the sheath retention groove 162 to confine the catheter sheath 158 while the cannula ready IV kit 130 is removed from its sterilized package. It will be noted that the catheter sheath 158 does not fully enclose the contoured central portion 104 of the cannula ready IV 100. The catheter sheath 158 provides a catheter access port 165 for egress of the catheter tube 116 and enclosed insertion needle 146 from the catheter sheath 158.

That is, as shown in FIGS. 5-6, the sheath and cover assembly 156 includes the catheter sheath 158 that includes the retention ring 164, the sheath retention groove 162 lockingly engages the retention ring 164, the pre-slit cannula diaphragm 122, the external male luer-type threads 128, the cylindrical housing 102, the catheter tube 116, and the insertion needle 146 are each confined by the threaded needle assembly cover 160 lockingly engaging with the external male luer-type threads 128 and the catheter sheath 158 lockingly engaging with the threaded needle assembly cover 160.

To remove the catheter ready IV kit 130 from the sheath and cover assembly 156, the threaded needle assembly cover 160 is held stationary while a downward pressure is applied to the catheter sheath 158 to disengage the retention ring 164 from the retention groove 162. With the catheter sheath 158 disengaged from the threaded needle assembly cover 160, the catheter sheath 158 is slid off catheter 116 and insertion needle 146. With the catheter sheath 158 removed, the contoured central portion 104 is held stationary while the threaded needle assembly cover 160 is unscrewed from the external male luer-type threads 128, which frees the catheter ready IV kit 130 for use, i.e., female threads 167 of the threaded needle assembly cover 160 are detached from the external male luer-type threads 128 of the luer-type connector site 110.

FIGS. 7-10 are provided to show the features of the split faux-cannula assembly tool 140. FIG. 7 shows a first fixture body 166 combining with a second fixture body 168 to form a cannula shaped body 170, which has a rounded and tapered lead in portion 172. The combination of the fixture bodies also provides a fixture shoulder 174. FIG. 8 shows that the combination of the first fixture body 166 with the second fixture body 168 provides a needle access aperture 176 size to accommodate passage of the insertion needle 146 (of FIG. 4).

As shown by FIG. 9, the first fixture body 166 provides an interlock feature 178 that communicates with an interlock feature 180 of the second fixture body 168. The interlocking features assure the relationship between the first fixture body 166 and the second fixture body 168 is maintained during the assembly of the catheter ready IV kit 130 (of FIG. 4).

The split faux-cannula assembly tool 140 is used during assembly of the catheter ready IV kit 130 to maintain integrity of the pre-slit cannula diaphragm 122. The tapered lead in portion 172 of the cannula shaped body 170 is inserted through an access slit of the pre-slit cannula diaphragm 122, and slid into the cannula chamber 150 of the cannula ready IV 100 (of FIG. 4). With the split faux-cannula assembly tool 140 position within the cannula ready IV 100, the insertion needle 146 is passed through the needle access aperture 176 and into communication with the catheter tube 116 (of FIG. 4). Prior to sliding the insertion needle 146 into its final relationship with catheter tube 116, the split faux-cannula assembly tool 140 is removed from the cannula chamber 150.

A comparison between FIGS. 11 and 12 shows that the prior art projects a discontinuous contour 58, which is more prone to irritation of the patient's skin. Skin irritation minimization is attained by the cannula ready IV 100 through the incorporation of a contoured and uninterrupted smooth surface 182, which undergoes a continuous decreasing diameter from the shoulder 126 through the distal end 118 of the catheter hub 112.

Accordingly, the present invention is directed to an apparatus for minimizing health risks for patients and healthcare providers during the administration of an IV. In accordance with one embodiment, the apparatus comprising a cylindrical housing (such as 102) having a contoured central portion (such as 104) disposed between a proximal end (such as 106) and a distal end (such as 108), with an open fluid transfer conduit (such as 114) extending there between. The proximal end provides a luer-type connector site (such as 110), and the distal end provides a catheter hub (such as 112); a catheter tube (such as 116) communicates with the fluid transfer conduit and extends from a distal end (such as 118) of the catheter hub. A pre-slit cannula diaphragm (such as 122) caps the fluid transfer conduit at a proximal end (such as 124) of the luer-type connector site. The luer-type connector site provides a shoulder (such as 126) and external male luer-type threads (such as 128) disposed between the shoulder and the diaphragm. The cylindrical housing provides an uninterrupted smooth surface (such as 182) of continuous decreasing diameter from the shoulder through the distal end of the catheter hub.

Figure 13:
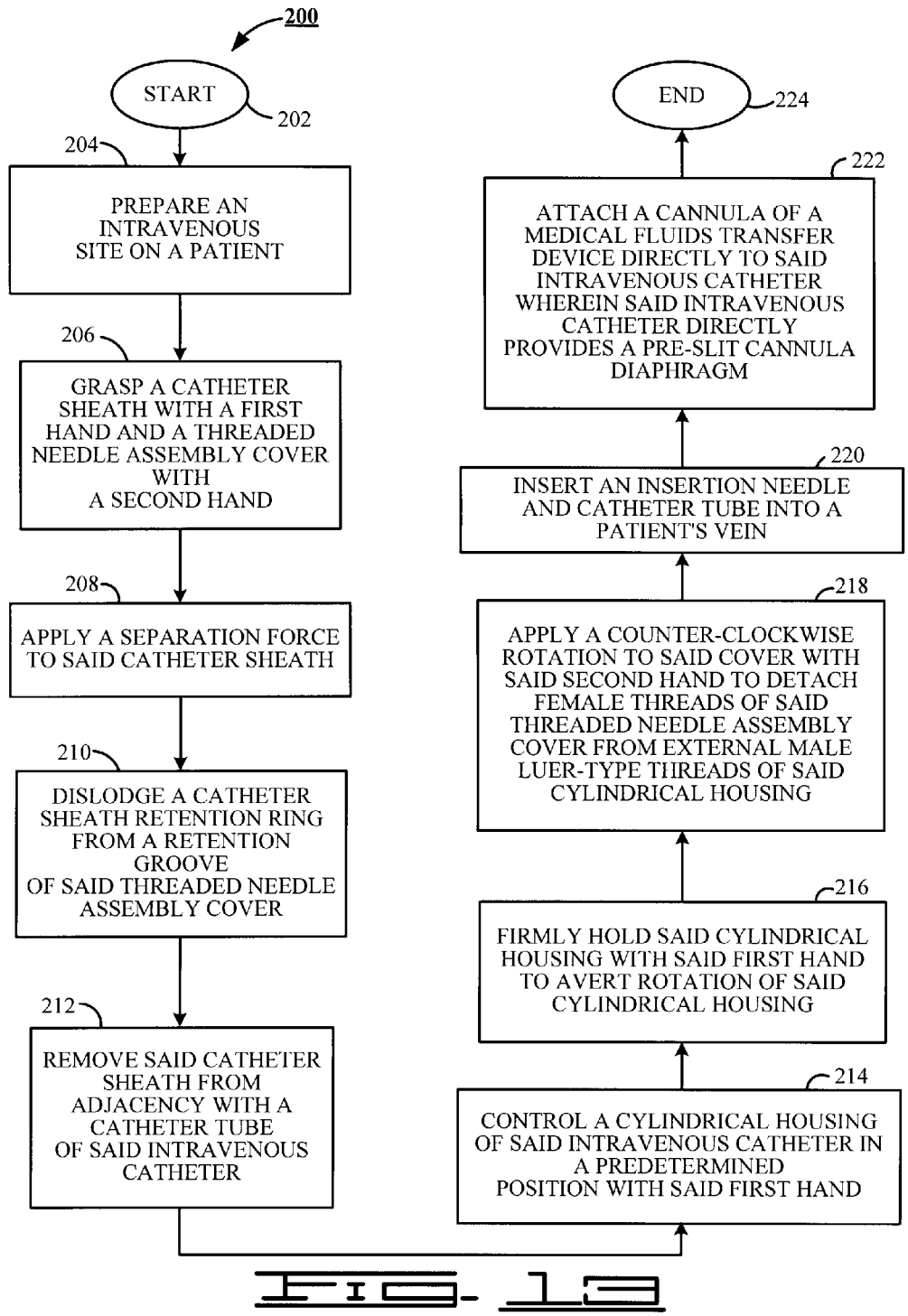
FIG. 13 is a flow diagram of a method of using the assembled IV kit of FIG. 4.

FIG. 13 shows a flow diagram of a method 200 of using a peripheral venous catheter with an integrated pre-slit cannula diaphragm (such as 100) commencing at start process step 202, and continuing at process step 204. At process step 204, the process continues with the preparation of an intravenous site on a patient (such as a patients hand H). At process step 206, the peripheral venous catheter with an integrated pre-slit cannula diaphragm is removed from a package (such as 156) by grasping a catheter sheath (such as 158) with a first hand, and a threaded needle assembly cover (such as 160) with a second hand. At process step 208, a separation force is applied to the catheter sheath, and at process step 210, a catheter sheath retention ring (such as 164) is dislodged from a retention groove (such as 162) of the threaded needle assembly cover.

At process step 212, the catheter sheath is removed from adjacency with a catheter tube (such as 116) of the peripheral venous catheter with an integrated pre-slit cannula diaphragm. At process step 214, a cylindrical housing (such as 102) of the peripheral venous catheter with an integrated pre-slit cannula diaphragm is controlled by the first hand to maintain the cylindrical housing in a predetermined position, and firmly held by the first hand to avert rotation of the cylindrical housing at process step 216. At process step 218, a counter-clockwise rotation is applied to the cover with the second hand to detach female threads (such as 167) of said threaded needle assembly cover from external male luer-type threads (such as 128) of the cylindrical housing.

The process continues at process step 220, with the insertion of an insertion needle (such as 146) and the catheter tube into a patient's vein. At process step 222, a cannula of a medical fluids transfer device is connected directly to the peripheral venous catheter with an integrated pre-slit cannula diaphragm, wherein the peripheral venous catheter with an integrated pre-slit cannula diaphragm provides a pre-slit cannula diaphragm (such as 122) for direct interface with the peripheral venous catheter with an integrated pre-slit cannula diaphragm, and the process concludes at end process step 224.

Figure 14:
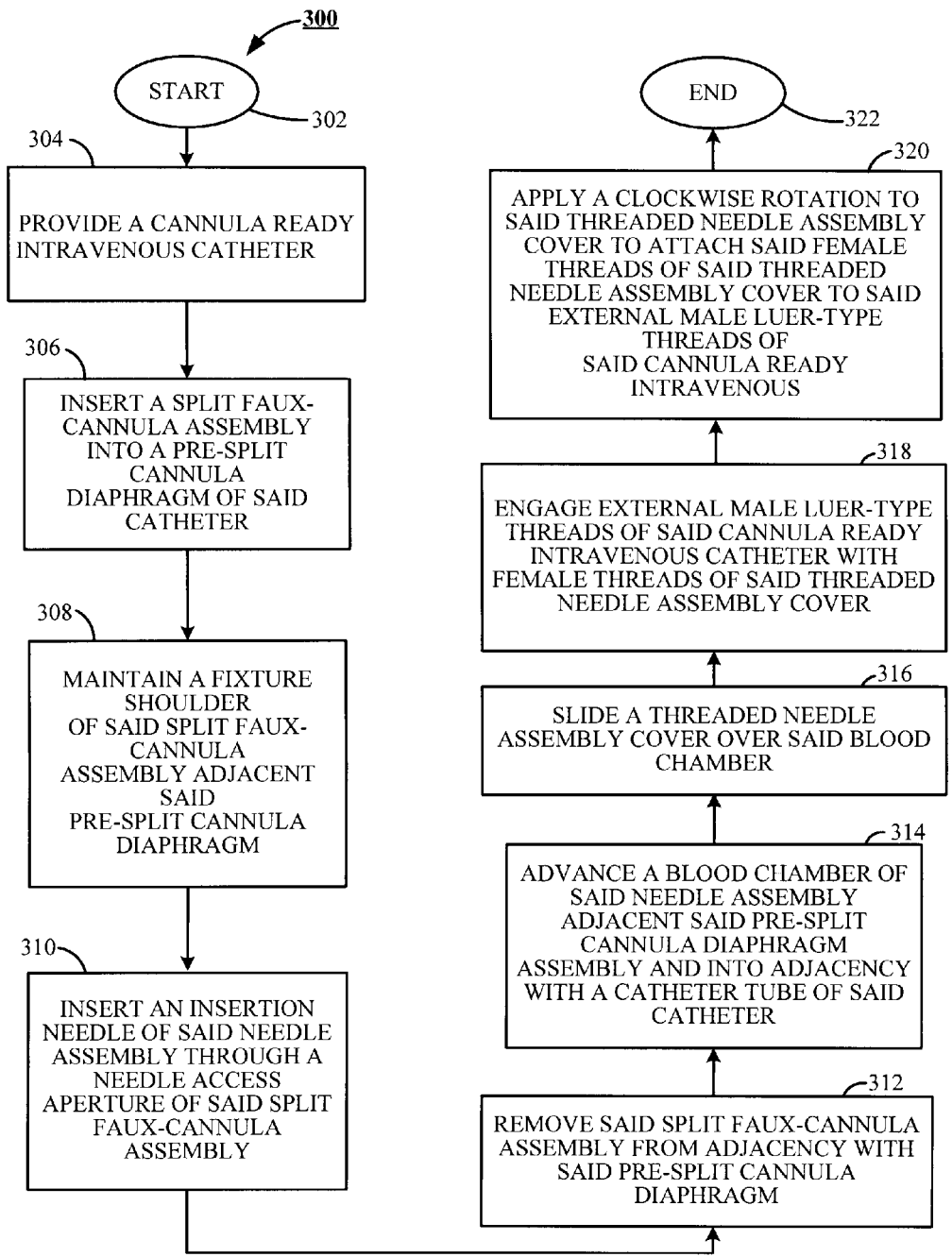
FIG. 14 is a flow diagram of a method of using the assembled IV kit of FIG. 4.

FIG. 14 shows a flow diagram of a method 300 of making a peripheral venous catheter with an integrated pre-slit cannula diaphragm (such as 100) commencing at start process step 302, and continuing at process step 304. At process step 304, the peripheral venous catheter with an integrated pre-slit cannula diaphragm is provided. At process step 306, a split faux-cannula assembly (such as 140) is inserted into a pre-split cannula diaphragm (such as 122) of the peripheral venous catheter with an integrated pre-slit cannula diaphragm.

At process step 308, a fixture shoulder (such as 174) of the split faux-cannula assembly is maintained adjacent the pre-split cannula diaphragm, while an insertion needle (such as 146) of a needle assembly (such as 136) is inserted through a needle access aperture (such as 176) of the split faux-cannula assembly at process step 310. At process step 312, the split faux-cannula assembly is removed from adjacency with the pre-split cannula diaphragm.

With the split faux-cannula assembly removed, at process step 314, a blood chamber (such as 142) of the needle assembly is advanced adjacent to the pre-split cannula diaphragm assembly and into adjacency with a catheter tube (such as 116) of the peripheral venous catheter with an integrated pre-slit cannula diaphragm. At process step 316, a threaded needle assembly cover (such as 160) is slid over the blood chamber, and at process step 318, external male luer-type threads (such as 128) of the peripheral venous catheter with an integrated pre-slit cannula diaphragm are engaged by female threads (such as 167) of the threaded needle assembly cover. At process step 320, a clockwise rotation is applied to the threaded needle assembly cover to attach the female threads of the threaded needle assembly cover to the external male luer-type threads of the peripheral venous catheter with an integrated pre-slit cannula diaphragm, and the process concludes at end process step 322.

It will be clear that the present invention is well adapted to attain the ends and advantages mentioned as well as those inherent therein. While presently preferred embodiments have been described for purposes of this disclosure, numerous changes may be made which will readily suggest themselves to those skilled in the art and which are encompassed by the appended claims.

What is claimed is:

1. An apparatus comprising;
a cylindrical housing provides a contoured central portion and a single luer-type connector site only, said luer-type connector site formed by and integral to said cylindrical housing on a proximal end of said cylindrical housing, a catheter hub formed integral to said cylindrical housing on a distal end of said cylindrical horsing adjacent the contoured central portion, and an open fluid transfer conduit disposed between said luer-type connector site and said catheter hub, wherein the single and only luer-type connector site provided by the cylindrical housing is a male luer-type connector site and the catheter hub is flange free, and further wherein a diameter of said cylindrical housing progressing from adjacent said mechanical connection feature through said distal end of said catheter hub has a continuously decreasing uninterrupted smooth surface, the continuously decreasing uninterrupted smooth surface mitigates skin irritation of a patient using the cylindrical housing;
a catheter tube confined by said open fluid transfer conduit, said catheter tube extending from a distal end of said catheter hub; and
a pre-slit cannula diaphragm capping said fluid transfer conduit at a proximal end of said luer-type connector site, in which said luer-type connector site forms a mechanical connection feature adjacent said pre-slit cannula diaphragm, and wherein a diameter of said cylindrical housing progressing from adjacent said mechanical connection feature through said distal end of said cylindrical housing decreases, and in which said mechanical connection feature is formed by and integral to said cylindrical housing.

2. The apparatus of claim 1, in which said mechanical connection feature comprises external male luer-type threads formed by and integral to said cylindrical housing.

3. The apparatus of claim 1, in which said cylindrical housing includes a shoulder provided by said luer-type connector site, said shoulder disposed between said mechanical connection feature and said distal end of said cylindrical housing, said shoulder formed by and integral to said cylindrical housing.

4. The apparatus of claim 1, further comprising a cannula chamber disposed between said catheter tube and said pre-split cannula diaphragm, said cannula chamber accommodates a corresponding cannula of a medical fluids transfer device.

5. The apparatus of claim 1, further comprising an insertion needle disposed within said catheter tube, wherein upon selectively inserting said insertion needle into a patient, said insertion needle provides access to a vein of said patient for penetration of said catheter tube into said vein of said patient.

6. The apparatus of claim 2, in which said cylindrical housing includes a shoulder provided by said luer-type connector site, said shoulder disposed between said mechanical connection feature and said distal end of said cylindrical housing.

7. The apparatus of claim 6, further comprising a cannula chamber disposed between said catheter tube and said pre-split cannula diaphragm, said cannula chamber accommodates a corresponding cannula of a medical fluids transfer device.

8. The apparatus of claim 7, further comprising a needle assembly interacting with said pre-slit cannula diaphragm, said needle assembly facilitating access through a wall of a patient's vein for penetration of said catheter tube into said vein.

9. The apparatus of claim 8, in which said needle assembly comprises an insertion needle disposed within said catheter tube, wherein upon selectively inserting said needle into a patient, said inserted insertion needle provides access to a vein of said patient for penetration of said catheter tube into said vein of said patient.

10. The apparatus of claim 9, in which said insertion needle comprises a fluid transfer channel, and wherein said needle assembly further comprises a blood chamber providing a needle hub and a collection chamber, said needle hub securing said inserted insertion needle in a predetermined fixed position relative to said blood chamber, and said blood chamber collecting fluid transferred from said vein through said fluid transfer channel.

11. The apparatus of claim 10, further comprises a pressure equalization member communicating with said blood chamber, said pressure equalization member assures that once said insertion needle penetrates through said wall of said vein, said fluid from said vein is able to flow freely into said collection chamber.

12. The apparatus of claim 11, in which said pressure equalization member comprises a filter medium disposed within a filter chamber of said pressure equalization member, said filter medium facilitating transfer of gaseous fluids while precluding passage of micro-organisms.

13. The apparatus of claim 12, further comprises a threaded needle assembly cover interacting with said external male luer-type threads, said threaded needle assembly cover constrains movement of said needle assembly relative to said pre-slit cannula diaphragm, when said threaded needle assembly cover is lockingly engaged with said external male luer-type threads.

14. The apparatus of claim 13 further comprises:
a sheath retention groove provided by said threaded needle assembly cover; and
a catheter sheath that includes a retention ring, said sheath retention groove lockingly engages said retention ring, said pre-slit cannula diaphragm, said external male luer-type threads, said cylindrical housing, said catheter tube, and said insertion needle are each confined by said threaded needle assembly cover lockingly engaging with said external male luer-type threads and said catheter sheath lockingly engaging with said threaded needle assembly cover.

* * * * *